United States Patent [19]

Olive

[11] Patent Number: 5,107,850

[45] Date of Patent: Apr. 28, 1992

[54] METHOD AND APPARATUS FOR CLASSIFYING AND TREATING CARDIAC ARRHYTHMIAS BASED ON ATRIAL AND VENTRICULAR ACTIVITY

[75] Inventor: Arthur L. Olive, Stacy, Minn.

[73] Assignee: Cardiac Pacemakers, Inc., St. Paul, Minn.

[21] Appl. No.: 608,532

[22] Filed: Nov. 2, 1990

[51] Int. Cl.$^5$ .............................................. A61B 5/04
[52] U.S. Cl. .............................. 128/705; 128/419 PG; 128/419 D
[58] Field of Search ............ 128/419 D, 419 PG, 705

[56] References Cited

U.S. PATENT DOCUMENTS

| | | | |
|---|---|---|---|
| 4,577,634 | 3/1986 | Gessman | 128/419 PG |
| 4,860,749 | 8/1989 | Lehmann | 128/419 PG |
| 4,944,298 | 7/1990 | Sholder | 128/419 PG |
| 4,971,058 | 11/1990 | Pless et al. | 128/419 D |

*Primary Examiner*—William E. Kamm
*Attorney, Agent, or Firm*—Fleit, Jacobson, Cohn, Price, Holman & Stern

[57] ABSTRACT

A method for classifying cardiac arrhythmias by examining the atrial and ventricular activity of the heart. The atrial contraction rate and ventricular contraction rate are compared with each other when the ventricular rate exceeds a preset value. When the atrial rate exceeds the ventricular rate, the regularity of the atrial rate, ventricular rate, and time interval between atrial contraction and ventricular contraction are determined. Regularity is determined by computing the standard deviation of a variable and comparing the standard deviation with a predetermined fractional value of the variable. A therapy routine is provided depending on the classification of a detected arrhythmia and the level of the ventricular contraction rate.

30 Claims, 6 Drawing Sheets

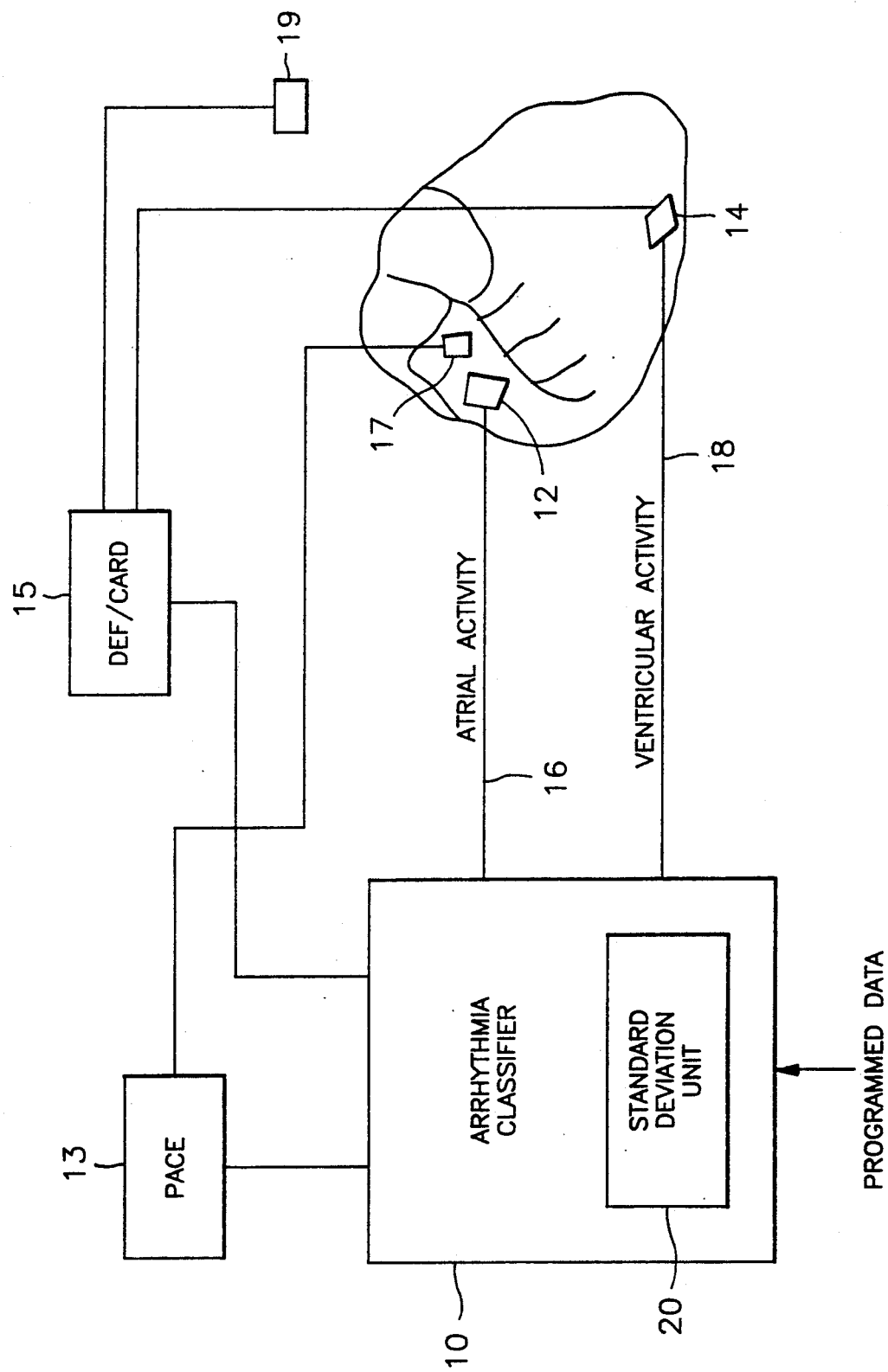

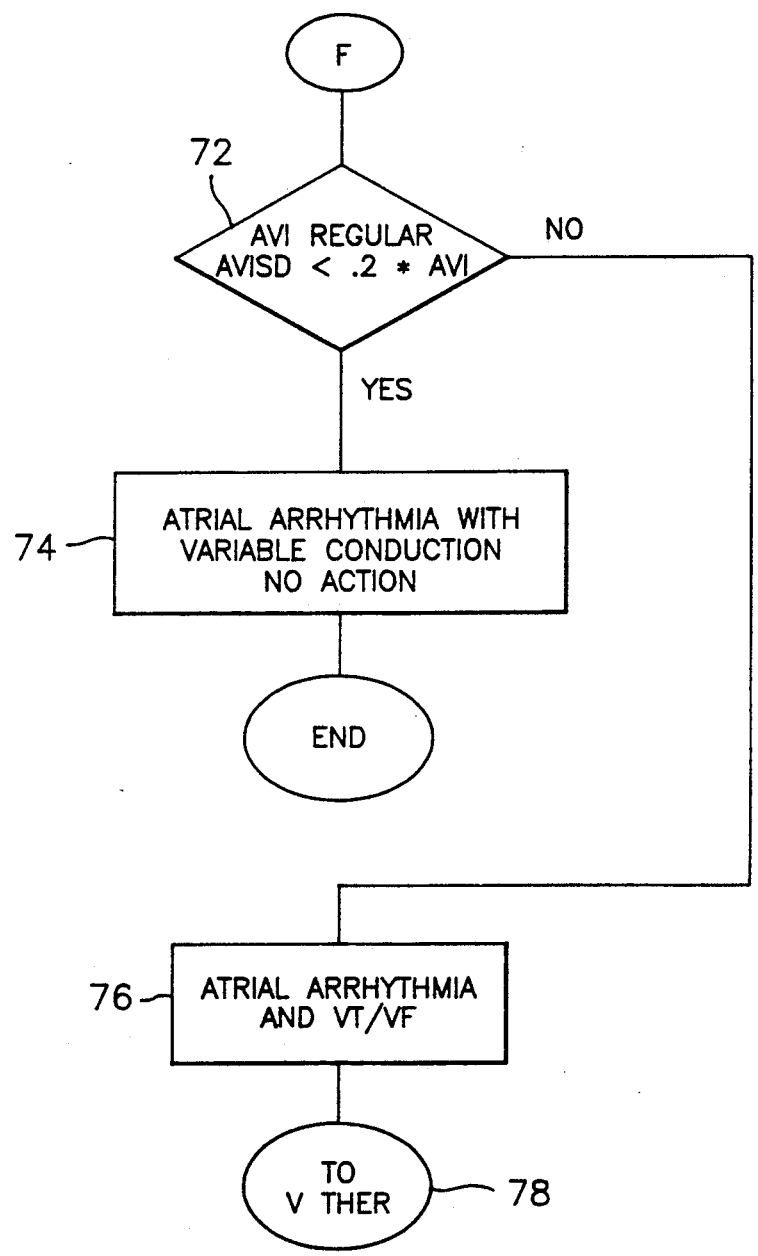

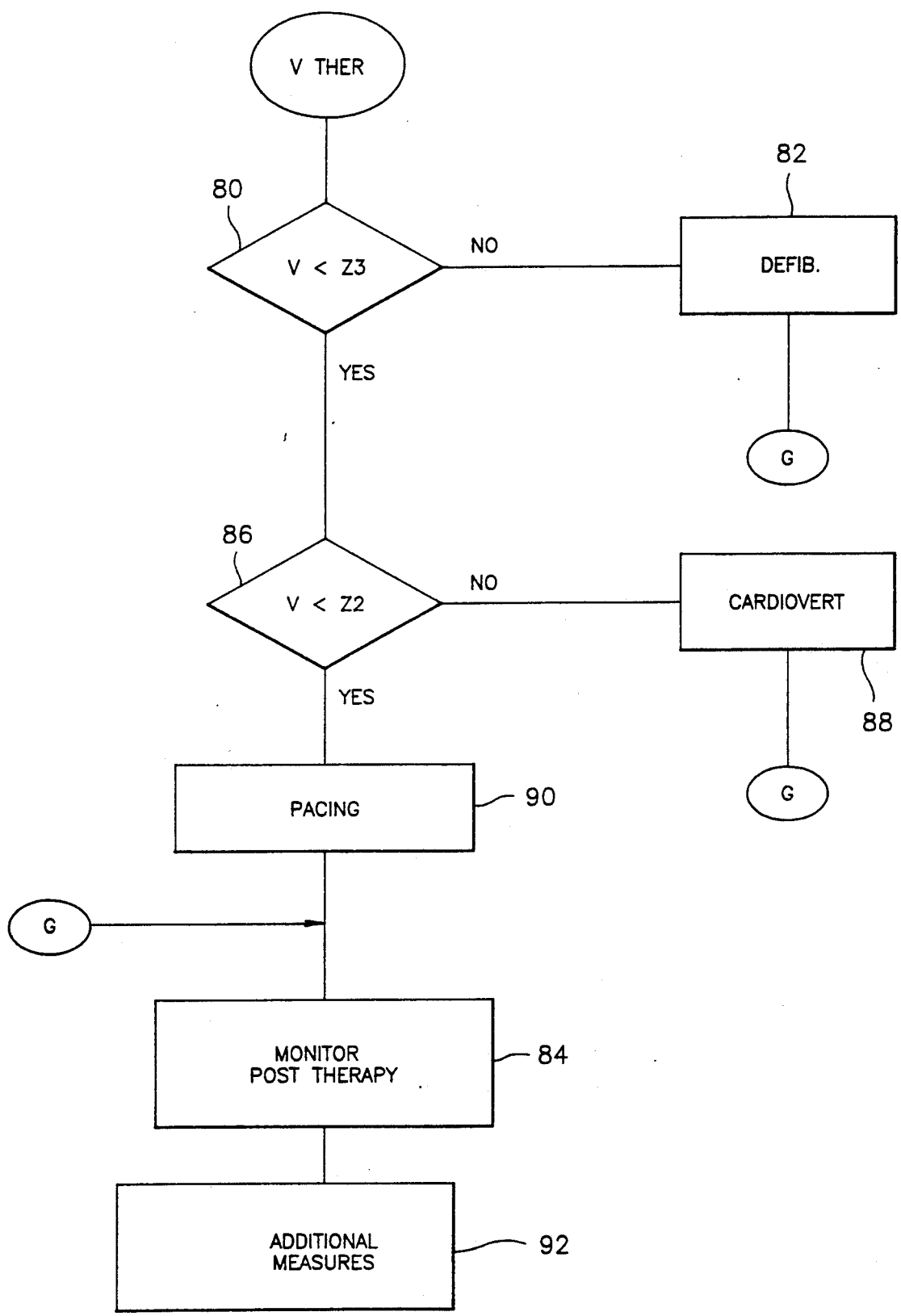

5,107,850

METHOD AND APPARATUS FOR CLASSIFYING AND TREATING CARDIAC ARRHYTHMIAS BASED ON ATRIAL AND VENTRICULAR ACTIVITY

BACKGROUND OF THE INVENTION

The present invention relates to an implantable cardioverter/defibrillator and more specifically to a method for discriminating atrial rhythms from ventricular rhythms.

In the field of cardiac monitoring and treatment systems, it is often necessary to distinguish the electrical activity in the atria from the electrical activity in the ventricles of the heart. One way to make this distinction is to provide widely separated ventricular leads so that the sources of the electrical signals taken from the heart are not detected by the same lead configuration. A critical disadvantage of this method is that in order to place the sensing leads in the appropriate positions, an invasive thoracotomy procedure is required.

Another method to discriminate sensed atrial electrical activity from sensed ventricular activity is through the use of cross-correlation and transfer function analysis of multiple single lead systems. However, this type of solution requires intensive and complex signal processing.

SUMMARY OF THE INVENTION

It is a primary object of the present invention to provide a method for classifying cardiac arrhythmias by discriminating between the electrical activity of the atria and ventricles.

It is an additional object of the present invention to provide a method for discriminating between atrial rhythms and ventricular rhythms using two transvenous endocardial standard pacing leads, one for sensing the atrial electrical activity and one for sensing ventricular electrical activity.

It is yet another object of the present invention to provide a method for classifying cardiac arrhythmias by discriminating between the electrical activity of the atria and ventricles without intensive signal processing.

Briefly, the present invention relates to a cardiac arrhythmia classifying algorithm which monitors the atrial and ventricular activity of the heart. The present invention is used to classify certain arrhythmias of the heart and to determine the appropriate therapy based on the type of arrhythmia detected. Initially, the ventricular contraction rate is compared with a preset value. If the ventricular rate is less than the preset value, no further action is taken. Otherwise, the ventricular and atrial contraction rates are compared with each other. Should the ventricular rate exceed the atrial rate, no further monitoring is performed and a therapy routine is commenced. However, if the atrial rate is greater than or equal to the ventricular rate, further processing occurs.

Specifically, if the atrial rate and ventricular rate are equal, the time interval between atrial contraction and ventricular contraction (AVI) is determined and compared with a preset value. If the AVI is less than or equal to the preset value, it is declared that a junctional tachycardia is occurring. Otherwise, if the atrial rate is greater than the ventricular rate, additional steps are taken such as computing the standard deviation of the ventricular and atrial rates, as well as the AVI to determine the regularity of these quantities. Classification of an arrhythmia is then based on the regularity and value of the ventricular rate, atrial rate, and the AVI.

The above and other objects and advantages will become more readily apparent when reference is made to the following description taken in conjunction with the accompanying drawings.

BRIEF DESCRIPTION OF THE DRAWINGS

FIG. 1 is a schematic block diagram of the cardiac classifier as used for classifying arrhythmias of the heart according to the present invention.

FIGS. 2A-2F are flow diagrams illustrating the cardiac classifying algorithm according to the present invention.

FIG. 3 is a flow diagram illustrating a therapy routine used in accordance with the cardiac classifying algorithm of the present invention.

DETAILED DESCRIPTION OF THE DRAWINGS

Figure 2A:
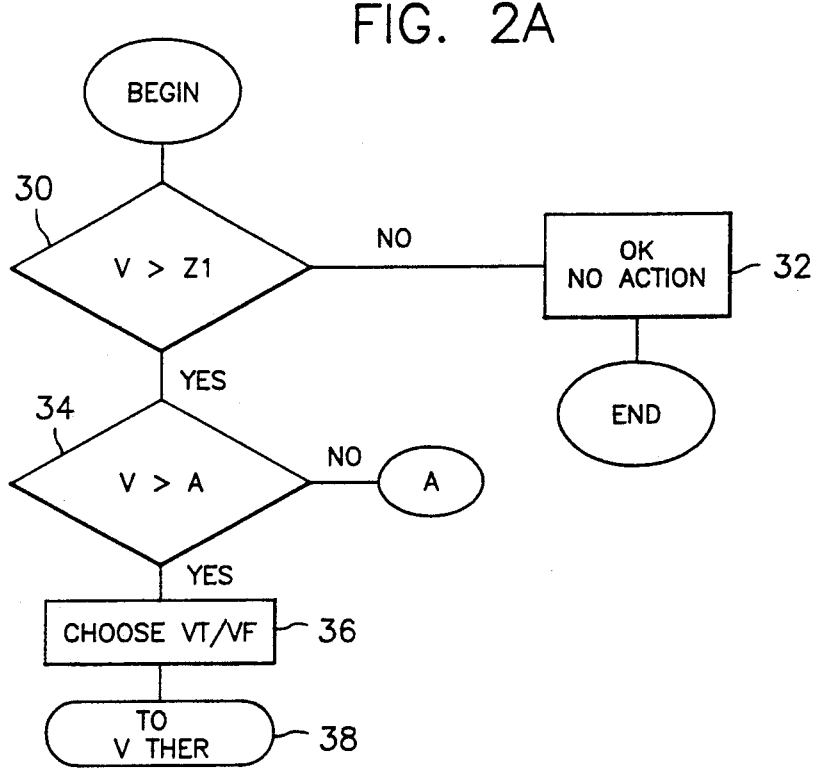

FIG. 1 illustrates the cardiac arrhythmia classifier according to the present invention as used for monitoring the electrical activity of the heart. The arrhythmia classifier is generally shown at 10 and is connected to an atrial sensing electrode 12 and a ventricular sensing electrode 14 via an atrial electrode lead 16 and a ventricular electrode lead 18, respectively. The electrodes 12 and 14 are preferable endocardial pacing type leads which are implanted appropriately to detect the electrical activity of the atria and ventricles, respectively, and more specifically sense atrial rate and ventricular rate, respectively. Atrial and ventricular rate data is processed by the classifier in terms of pulses per minute (PPM).

In addition, the classifier 10 can be used in conjunction with a pacemaking unit 13 and a defibrillator/cardioverter 15 each of which are connected to the classifier 10. In this regard, the pacemaker 13 is connected to a pacemaker electrode 17 and the defibrillator/cardioverter 15 is connected to a subcutaneous patch electrode 19 (ground) and the ventricular electrode 14 for delivering defibrillation or cardioversion energies through the myocardium. The particular types and placement of the pacemaking and defibrillation electrodes are not an essential part of the present invention.

The classifier 10 is preferably embodied as a microprocessor or computer. The classifying algorithm is embodied as a software program which is run by the computer or microprocessor embodying the classifier 10. The classifier 10 also is capable of computing the various time intervals from the data sensed by the electrodes 12 and 14 such as the time interval between atrial systole and ventricular systole (AVI) and the sinus AVI. As is well known in the art, sinus AVI is the time interval between atrial and ventricular contractions during normal sinus rhythm. This interval is determined on a per patient basis at the time of implantation and may be revised during the course of normal follow up tests. The classifier includes a device or another algorithm for computing the standard deviation (SD) of input signals. The standard deviation unit is shown at 20 and is provided to compute the standard deviation of the atrial and ventricular rates as well as the standard deviation of the AVI. It is understood by those skilled in the art that approximations to the standard deviation exist which require less computation and may be employed in the algorithm of the present invention.

The classifier also receives as input programmable data which is used by the algorithm. Table 1 below lists the examples of the programmable data.

TABLE 1

| PROGRAMMABLE DATA | |
|---|---|
| VARIABLE | MEANING |
| TACHY RATE | Threshold rate above which tachycardia is declared. |
| STABILITY MEASURE | The stability measure of a measurement is defined as the deviation of a measurement divided by the measurement. |
| MEAN SEPARATION | The sum of the standard deviations of the atrial and ventricular rates, divided by 2 = mean separation. |
| RATE ZONES | Zones or ranges of rate levels in which certain therapeutic measures are taken. (Z1, Z2, and Z3) |
| CROSSOVER RATE | A threshold rate value for ventricular rate. Ventricular rates above this value are determined to be hemodynamically unstable and are treated as ventricular tachycardia with no further algorithm steps. |

Rate zones may be established on a per patient basis at the time of implantation and may be changed during follow up in response to changes in patient condition or medication as is deemed appropriate by the attending physician. A standard value for Z1 is 100 ppm, which is a common definition of a minimum tachycardia rate. Possible values for Z2 and Z3 are 150 ppm and 250 ppm, respectively. This establishes three zones for therapy:

Z1: 100 to 149 ppm; anti-tachycardia pacing
Z2: 150 to 249 ppm; cardioversion
Z3: 250 ppm and up; defibrillation FIGS. 2A-2F illustrate the cardiac arrhythmia classifying algorithm according to the present invention. The atrial rate, ventricular rate, AVI and standard deviations of atrial rate, ventricular rate and AVI are continuously averaged over a predetermined time sample period. This time sample period is set to the toleration of the device, such as the time necessary to charge a defibrillation capacitor. Approximately 15 seconds are needed to charge conventional defibrillation capacitors. However, the toleration can be set according to other factors. The atrial rate, ventricular rate and AVI data is fed from the electrodes 12 and 14 to the cardiac classifier which implements the arrhythmia classifying algorithm on a cardiac cycle basis.

The algorithm begins in step 30 by comparing the ventricular rate (V) with the programmed threshold value Z1. If the ventricular rate V is less than Z1, no further action is taken as shown in step 32. However, if the ventricular rate V is greater than Z1, a comparison is made between the ventricular rate V and the atrial rate A in step 34. If the ventricular rate is greater than the atrial rate and the difference is greater than the mean separation, it is declared in step 36 that either ventricular tachycardia or ventricular fibrillation is occurring. Thereafter, the algorithm enters the ventricular therapy routine V THER which will be described in detail hereinafter in conjunction with FIG. 3.

Figure 2B:
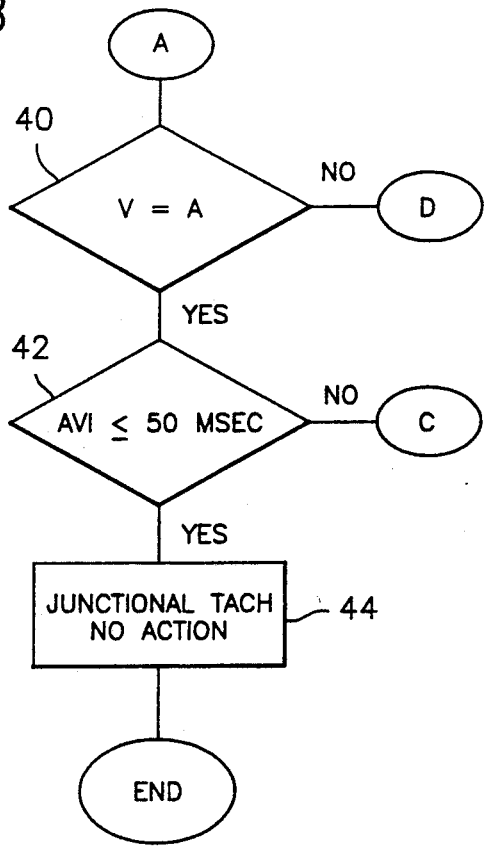
Figure 2C:
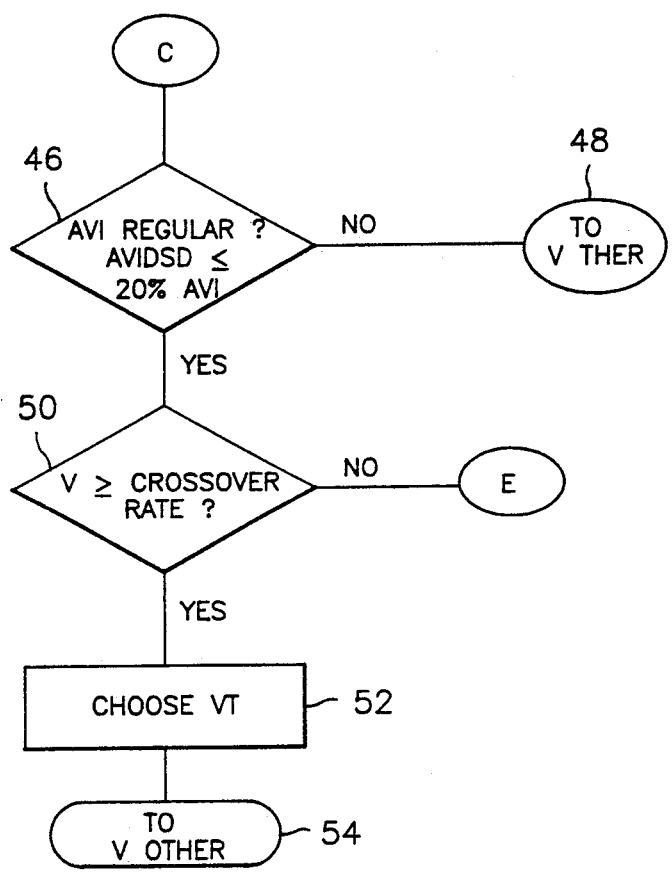

If the ventricular rate is less than or equal to the atrial rate, the algorithm jumps to the steps illustrated in FIG. 2B. First, it is determined whether the ventricular and atrial rates are equal in step 40. Equality of atrial and ventricular rates is determined by comparing the absolute value of difference in rate to the mean separation. If the difference is less than the means separation the rates are treated as equal. If the rates are not equal, then it is determined that the atrial rate is greater than the ventricular rate and the routine jumps to the steps shown in FIG. 2E. Otherwise, if the ventricular and atrial rates are equal, step 42 is initiated in which a comparison of the time interval between atrial systole and ventricular systole AVI is less than or equal to 50 msecs. If the AVI is greater than 50 msecs, then the steps shown in FIG. 2C are performed. Otherwise, it is declared that there is a junctional tachycardia condition as shown in step 44 and no action is taken.

FIG. 2C illustrates the measures taken if the AVI is greater than 50 msecs. In step 46, it is determined whether the AVI is regular by comparing the standard deviation of the AVI (AVISD) with 20% of the value of AVI. If the standard deviation of AVI is greater than 20% of AVI, indicating that the AVI is irregular, the algorithm jumps to the V THER routine shown in FIG. 3 in step 48. All comparisons of rate, intervals and standard deviations are based on averages determined over the past several seconds. This determination of the regularity of the AVI works since if AVI is irregular, the atria and ventricles are not in synchronization during which there is possibly atrial flutter with coincident ventricular tachycardia. Atrial arrhythmias may produce minor irregularity of the AVI. Because the ventricle is being driven by the atrium the irregularity will be small compared to that observed during an independent ventricular rhythm.

If the AVISD is less than or equal to 20% of AVI indicating that the AVI is regular, step 50 is performed in which the ventricular rate is compared with the programmed value of the CROSSOVER RATE. When the ventricular rate is greater than or equal to the CROSSOVER RATE, it is declared that ventricular tachycardia is occurring in step 52 and the V THER routine is entered from step 54. If the ventricular rate V is less than the CROSSOVER RATE, the algorithm jumps to the steps shown in FIG. 2D.

Figure 2D:
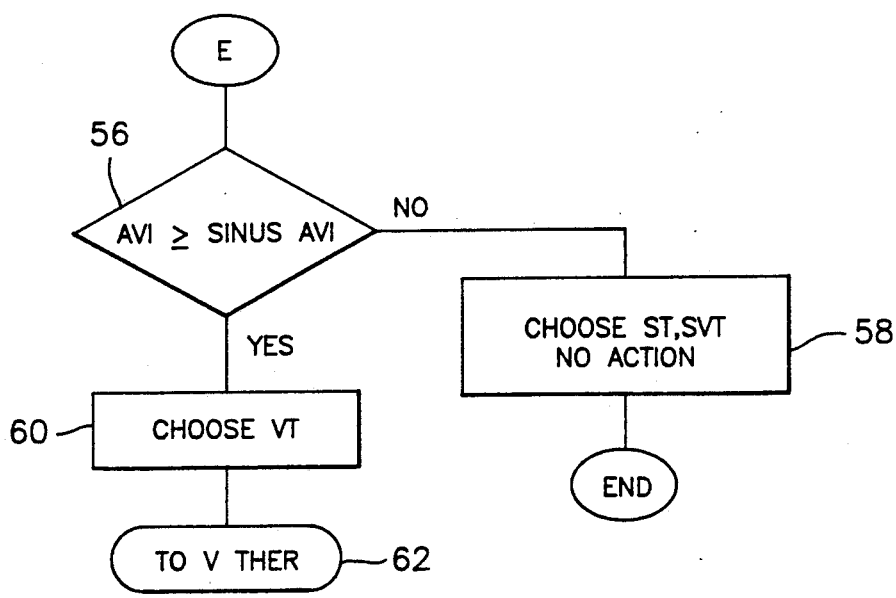

When it is determined in step 50 that the ventricular rate is less than the CROSSOVER RATE, step 56 in FIG. 2D is performed. In step 56, a comparison is made between the AVI and the sinus AVI. If the AVI is less than the sinus AVI, then it is declared that either ST (sinus tachycardia) or SVT (supra ventricular tachycardia) is occurring in step 58 and no action is taken. Otherwise, if AVI is greater than or equal to sinus AVI, then it is declared that ventricular tachycardia is occurring in step 60 and the algorithm jumps to the V THER routine from step 62.

Figure 2E:
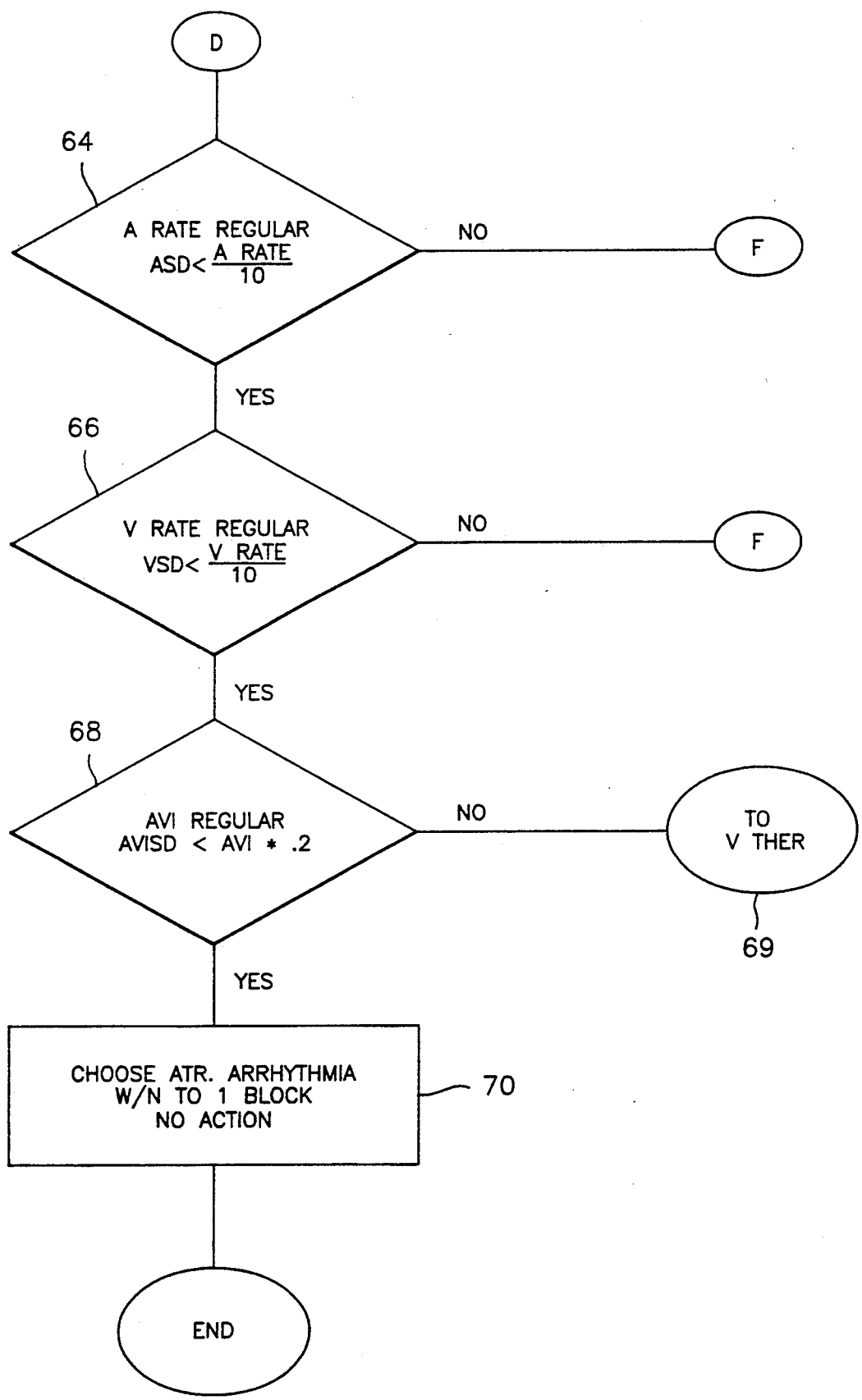

Referring briefly back to FIG. 2B, if it is determined that the ventricular rate is not equal to the atrial rate in step 40 (meaning the atrial rate is greater than the ventricular rate), the algorithm jumps to the steps in FIG. 2E. First, in step 64 it is determined whether the atrial rate is regular. This is accomplished by comparing the standard deviation of the atrial rate ASD with one-tenth of the value of the atrial rate. If the ASD is greater than or equal to the atrial rate divided by ten indicating that the atrial rate is irregular, the algorithm jumps to the steps shown in FIG. 2F. Otherwise, if the ASD is less than the atrial rate divided by ten, step 66 is performed in which it is determined whether the ventricular rate is regular. At this point, given that it has been determined so far that the atrial rate is greater than the ventricular rate and that the atrial rate is regular, the most likely diagnosis is that the heart is in ST, AT (atrial tachycardia) or atrial flutter.

To determine the regularity of the ventricular rate in step 66, the standard deviation of the ventricular rate VSD is compared with one tenth the value of the ventricular rate. Similar to step 64, if the VSD is greater than or equal to the ventricular rate divided by ten indicating that the ventricular rate is irregular, the algorithm jumps to the steps shown in FIG. 2F. If both the ventricular and atrial rates are determined to be regular, the most likely diagnosis is that the heart is in ST, AT, or atrial flutter with a block. If the ventricular rate is determined to be regular in step 66, then it is determined whether the AVI is regular in step 68 using the same standard as in step 46. If the AVI is regular, it is declared in step 70 that the heart is in atrial arrhythmia and no action is taken. Otherwise, if the atrial and ventricular rates are regular but the AVI is not regular, the atria and ventricles are not in synchronization and it is determined that there is an atrial arrhythmia with coincident ventricular tachycardia. Therefore, the algorithm jumps to the V THER routine as shown in step 69 in FIG. 3.

If the atrial rate is greater than the ventricular rate and either the atrial rate or ventricular rate is irregular, the steps illustrated in FIG. 2F are performed. In addition if the heart is in SVT and the atrial rate is not regular, then the ventricular rate should also not be regular and the steps in FIG. 2F are also reached. Preliminarily, once the steps in FIG. 2F are reached, the heart condition can be approximately diagnosed as being a ventricular tachycardia. However, in step 72 it is determined whether the AVI is regular. If the AVI is determined to be regular in step 72, it is declared in step 74 that the heart is in atrial arrhythmia with a variable conduction block and no further action is taken. Particularly, if the AVI is regular and the atrial rate is greater than the ventricular rate, an atrial rate arrhythmia is indicated with the ventricular response being limited by the refractory period of the AV node.

On the other hand, if the AVI is not regular as determined in step 72, then it is declared in step 76 that the heart is in an atrial arrhythmia with coincident ventricular tachycardia or ventricular fibrillation. Specifically, if the atrial rate is greater than the ventricular rate, the atrial rate or the ventricular rate is irregular, and the AVI is irregular, then it is diagnosed that the heart is in an atrial arrhythmia with coincident ventricular tachycardia. Subsequent to the declaration in step 76, the V THER routine illustrated in FIG. 3 is executed as evidenced by step 78.

FIG. 3 illustrates the V THER routine which is executed upon determining one of a number of conditions throughout the classifying algorithm. Specifically, the V THER routine is reached in one of several ways:

(1) via step 38 in FIG. 2A when the ventricular rate is greater than the atrial rate; via step 48 in FIG. 2C when the atrial and ventricular rates are equal, the AVI is greater than 50 msecs, and the AVI is irregular;

(2) via step 54 in FIG. 2C when the ventricular and atrial rates are equal and the AVI is greater than 50 msec and regular and the ventricular rate is greater than the CROSSOVER RATE;

(3) via step 62 in FIG. 2D when the atrial and ventricular rates are equal, the AVI is greater than 50 msecs, the AVI is regular, the ventricular rate is less than the CROSSOVER RATE, and the AVI is greater than or equal to the sinus AVI;

(4) via step 69 when the atrial rate is greater than the ventricular rate, both the atrial and ventricular rates are regular, and the AVI is irregular; or (5) via step 78 when the atrial rate is greater than the ventricular rate, either the atrial rate or ventricular rate is irregular, and the AVI is irregular.

The arrhythmia classifier 10 triggers the pacemaking unit 13 or the defibrillation/cardioversion unit 15 to deliver therapeutic electrical energy to the heart depending on the classification of the arrhythmia.

Initially in the V THER routine, the ventricular rate is compared with zone limit Z3 in step 80. If the ventricular rate is greater than or equal to this upper limit, then it is determined that the heart is in ventricular fibrillation and the heart is supplied with a defibrillation shock in step 82 via the defibrillation/cardioversion unit 15. Thereafter, the routine enters a post therapy monitoring step 84. On the other hand, if the ventricular rate is less than the zone limit Z3, the ventricular rate is compared with a lower limit Z2 in step 86. Thus, if the ventricular rate is greater than Z2 but less than Z3, it is determined that the heart requires a cardioversion shock which is supplied via the defibrillation/cardioversion unit 15 in step 88. Finally, if the ventricular rate is less than both Z2 and Z3, it is determined that the heart requires a pacing pulse (or series thereof) which is delivered via the pacemaking unit 13 in step 90. Subsequent to the application of the measures in steps 82, 88 and 90, the routine enters the post therapy monitoring step 84. Additional measures shown in step 92 can be taken including further monitoring, and additional or repeated therapy.

The above description is intended by way of example only and is not intended to limit the present invention in any way except as set forth in the following claims.

I claim:

1. A method for classifying cardiac arrhythmias comprising the steps of:

sensing the electrical activity of an atrium and a ventricle of the heart;

determining the ventricular rate of contraction and the atrial rate of contraction;

comparing the ventricular rate with a preset threshold value;

comparing the ventricular rate with the atrial rate if the ventricular rate exceeds said preset threshold value; and classifying the rhythm of the heart as ventricular fibrillation or ventricular tachycardia if the ventricular rate is greater than the atrial rate.

2. The method of claim 1, and further comprising the steps of:

computing the time interval between atrial contraction and ventricular contraction (AV);

comparing said AV time interval with a predetermined time interval value if said atrial rate is equal to said ventricular rate; and classifying the rhythm of the heart as a junctional tachycardia if said ventricular and atrial rates are equal and said AV time interval is less than or equal to said predetermined time interval value.

3. The method of claim 2, and further comprising the steps of:

determining whether said AV time interval is regular if said AV time interval is greater than said predetermined time interval value;

comparing the ventricular rate with a predetermined crossover rate value if said AV time interval is regular; and classifying the rhythm of the heart as a ventricular tachycardia if said ventricular rate is greater than or equal to said predetermined crossover rate value.

4. The method of claim 3, and further comprising the steps of:

determining the time interval (SAV) between sinus atrial contraction and ventricular contraction to distinguish ventricular tachycardia from another condition;

comparing said AV time interval with said SAV time interval; and classifying the rhythm of the heart as ventricular tachycardia if said AV time interval is greater than or equal to said SAV time interval and otherwise classifying the rhythm of the heart as said another condition.

5. The method of claim 4, and further comprising the steps of:

providing a lower rate limit of a first rate zone and a lower rate limit of a second rate zone, said lower limit of said second rate zone being greater than said lower rate limit of said second rate zone;

providing a lower rate limit of a third rate zone being greater than said lower rate limit of said second rate zone;

comparing said ventricular contraction rate with said lower rate limit of said third rate zone if said AV time interval is greater than or equal to said SAV time interval; and comparing said ventricular contraction rate with said lower rate limit of said second rate zone if said ventricular rate is less than said lower rate limit of said third rate zone.

6. The method of claim 3, and further comprising the step of computing the standard deviation of said AV time interval, and wherein said step of determining whether said AV time interval is regular comprises the steps of:

computing a predetermined fraction of said AV time interval;

comparing said standard deviation of said AV time interval with said predetermined fraction; and declaring said AV time interval to be regular if said standard deviation of said AV time interval is less than said predetermined fraction, and otherwise declaring said AV time interval to be irregular.

7. The method of claim 3, and further comprising the steps of:

providing a lower rate limit of a first rate zone and a lower rate limit of a second rate zone, said lower rate limit of said second rate zone being greater than said lower rate limit of said first rate zone;

providing a lower rate limit of a third rate zone that is greater than said lower rate limit of said second rate zone;

comparing said ventricular contraction rate with said lower rate limit of said third rate zone if said ventricular contraction rate is greater than said ventricular crossover rate to determine if the rhythm of the heart is ventricular fibrillation; and comparing said ventricular contraction rate with said lower rate limit of said second rate zone if said ventricular rate is less than said lower rae limit of said third rate zone to determine if the heart is in a fast rhythm or an arrhythmia requiring a cardioverting shock.

8. The method of claim 2, and further comprising the steps of:

determining whether said atrial rate is regular if the ventricular rate is less than said atrial rate;

determining whether said ventricular rate is regular if said atrial rate is determined to be regular;

said steps of determining whether the atrial rate is regular and determining whether the ventricular rate is regular for establishing if the heart rhythm is sinus tachycardia or an atrial arrhythmia;

further determining whether said AV time interval is regular if said ventricular rate is determined to be regular; and classifying the rhythm of the heart as an atrial arrhythmia if said step of further determining determines that said AV time interval is regular.

9. The method of claim 8, and further comprising the steps of:

further determining whether said AV time interval is regular if either one of said ventricular or atrial rates is determined to be irregular to distinguish sinus tachycardia from atrial arrhythmia as the rhythm of the heart; and classifying the rhythm of the heart as an atrial arrhythmia with conduction problems if said step of further determining determines that said AV time interval is regular and otherwise classifying the rhythm of the heart as an atrial arrhythmia coincident with ventricular tachycardia or ventricular fibrillation.

10. The method of claim 9, and further comprising the step of computing the standard deviation of said AV time interval, and wherein said step of further determining whether said AV time interval is regular further comprises the steps of:

computing a predetermined fraction of said AV time interval;

comparing said standard deviation of said AV time interval with said predetermined fraction; and declaring said AV time interval to be regular if said standard deviation of said AV time interval is less than said predetermined fraction, and otherwise declaring said AV time interval to be irregular.

11. The method of claim 9, and further comprising the steps of:

providing a lower rate limit of a first rate zone and a lower rate limit of a second rate zone, said lower rate limit of said second rate zone being greater than said lower rate limit of said first rate zone;

providing a lower rate limit of a third rate zone being greater than said lower rate limit of said second rate zone;

comparing said ventricular contraction rate with said lower rate limit of said third rate zone if said step of further determining determines that said AV interval is irregular; and comparing said ventricular contraction rate with said lower rate limit of said second rate zone if said ventricular rate is less than said lower rate limit of said third rate zone.

12. The method of claim 8, and further comprising the step of computing the standard deviation of said atrial contraction rate and said ventricular contraction rate, and wherein said step of determining whether said atrial rate is regular comprises the steps of:

comparing said standard deviation of said atrial contraction rate with a predetermined fraction of said atrial rate; and declaring said atrial rate to be regular if said standard deviation of said atrial rate is less than said predetermined fraction of said atrial rate, and otherwise declaring said atrial contraction rate to be irregular; and wherein said step of determining whether said ventricular rate is regular comprises the steps of:

comparing said standard deviation of said ventricular contraction rate with a predetermined fraction of said ventricular contraction rate; and declaring said atrial rate to be regular if said standard deviation of said ventricular contraction rate is less than said predetermined fraction of said ventricular contraction rate, and otherwise declaring said ventricular contraction rate to be irregular.

13. The method of claim 8, and further comprising the step of computing the standard deviation of said AV time interval, and wherein said step of determining whether said AV time interval is regular further comprises the steps of:

computing a predetermined fraction of AV said time interval;

comparing said standard deviation of said AV time interval; and declaring said AV time interval to be regular if said standard deviation of said AV time interval is less than said predetermined fraction, and otherwise declaring said AV time interval to be irregular.

14. The method of claim 8, and further comprising the steps of:

providing a lower rate limit of a first rate zone and a lower rate limit of a second rate zone, said lower rate limit of said second rate zone being greater than said lower rate limit of said first rate zone;

providing a lower rate limit of a third rate zone being greater than said lower rate limit of said second rate zone;

comparing said ventricular contraction rate with said lower rate limit of said third rate zone if said AV time interval is determined to be irregular to determine if the rhythm of the heart is ventircular fibrillation; and comparing said ventricular contraction rate with said lower rate limit of said second rate zone if said ventricular rate is less than said lower rate limit of said third rate zone to determine if the heart is in a fast rhythm or an arrhythmia requiring a cardioverting shock.

15. The method of claim 2, and further comprising the steps of:

providing a lower rate limit of a first rate zone and a lower rate limit of a second rate zone, said lower rate limit of said second rate zone being greater than said lower rate limit of said first rate zone;

providing a lower rate limit of a third rate zone being greater than said lower rate limit of said second rate zone;

comparing said ventricular contraction rate with said lower rate limit of said third rate zone if said ventricular contraction rate is greater than said atrial contraction rate to determine if the rhythm of the heart is ventricular fibrillation; and comparing said ventricular contraction rate with said lower rate limit of said second rate zone if said ventricular rate is less than said lower rate limit of said third rate zone to determine if the heart is in a fast rhythm or an arrhythmia requiring a cardioverting shock.

16. A method for classifying cardiac arrhythmias and delivering therapy to the heart comprising the steps of:

sensing the electrical activity of an atrium and a ventricle of the heart;

determining the ventricular rate of contraction and the atrial rate of contraction;

comparing the ventricular rate with a preset threshold value;

comparing the ventricular rate with the atrial rate if the ventricular rate exceeds said preset threshold value;

classifying the rhythm of the heart as ventricular fibrillation or ventricular tachycardia if the ventricular rate is greater than the atrial rate;

computing the time interval between atrial contraction and ventricular contraction (AV);

comparing said AV time interval with a predetermined time interval value if said atrial rate is equal to said ventricular rate;

classifying the rhythm of the heart as a junctional tachycardia if said ventricular and atrial rates are equal and said AV time interval is less than or equal to said predetermined time interval value;

providing a lower rate limit of a first rate zone and a lower rate limit of a second rate zone, said lower rate limit of said second rate zone being greater than said lower rate limit of said first rate zone;

providing a lower rate limit of a third rate zone being greater than said lower rate limit of said second rate zone;

comparing said ventricular contraction rate with said lower rate limit of said third rate zone if said ventircular contraction rate is greater than said atrial contraction rate to determine if the rhythm of the heart is ventricular fibrillation;

comparing said ventricular contraction rate with said lower rate limit of said second rate zone if said ventricular rate is less than said lower rate limit of said third rate zone to determine if the heart is in a fast rhythm or an arrhythmia requiring a cardioverting shock;

delivering defibrillation pulses to the heart if said ventricular contraction rate is greater than said lower rate limit of said third rate zone;

delivering cardioverting pulses to the heart if said ventricular contraction rate is greater than said lower rate limit of said second rate zone and less than said lower rate limit of said third rate zone; and delivering pacing pulses to the heart if said ventricular contraction rate is less than said lower rate limit of said second rate zone.

17. A method for classifying cardiac arrhythmias and delivering therapy to the heart comprising the steps of:

sensing the electrical activity of an atrium and a ventricle of the heart;

determining the ventricular rate of contraction and the atrial rate of contraction;

comparing the ventricular rate with a preset threshold value;

comparing the ventricular rate with the atrial rate if the ventricular rate exceeds said preset threshold value;

classifying the rhythm of the heart as ventricular fibrillation or ventricular tachycardia if the ventricular rate is greater than the atrial rate;

computing the time interval between atrial contraction and ventricular contraction (AV);

comparing said AV time interval with a predetermined time interval value if said atrial rate is equal to said ventricular rate;

classifying the rhythm of the heart as a junctional tachycardia if said ventricular and atrial rates are equal and said AV time interval is less than or equal to said predetermined time interval value;

determining whether said AV time interval is regular if said AV time interval is greater than said predetermined time interval value;

comparing the ventricular rate with a predetermined crossover rate value if said AV time interval is regular;

classifying the rhythm of the heart as a ventricular tachycardia if said ventricular rate is greater than or equal to said predetermined crossover rate value;

providing a lower rate limit of a first rate zone and a lower rate limit of a second rate zone, said lower rate limit of said second rat zone being greater than said lower rate limit of said first rate zone;

providing a lower rate limit of a third rate zone that is greater than said lower rate limit of said second rate zone;

comparing said ventricular contraction rate with said lower rate limit of said third rate zone f said ventricular contraction rate is greater than said ventricular crossover rate to determine if the rhythm of the heart is ventricular fibrillation;

comparing said ventricular contraction rate with said lower rate limit of said second rate zone if said ventricular rate is less than said lower rate limit of said third rate zone to determine if the heart is in a fast rhythm or an arrhythmia requiring a cardioverting shock;

delivering defibrillation pulses to the heart if said ventricular contraction rate is greater than said lower rate limit of said third rate zone;

delivering cardioverting pulses to the heart if said ventricular contraction rate is greater than said lower rate limit of said second rate zone and less than said lower rate limit of said third rate zone; and delivering pacing pulses to the heart if said ventricular contraction rate is less than said lower rate limit of said second rate zone.

18. A method for classifying cardiac arrhythmias and delivering therapy to the heart comprising the steps of:

sensing the electrical activity of an atrium and a ventricle of the heart;

determining the ventricular rate of contraction and the atrial rate of contraction;

comparing the ventricular rate with a preset threshold value;

comparing the ventricular rate with the atrial rate if the ventricular rate exceeds said preset threshold value;

classifying the rhythm of the heart as ventricular fibrillation or ventricular tachycardia if the ventricular rate is greater than the atrial rate;

computing the time interval between atrial contraction and ventricular contraction (AV);

comparing said AV time interval with a predetermined time interval value if said atrial rate is equal to said ventricular rate;

classifying the rhythm of the heart as a junctional tachycardia if said ventricular and atrial rates are equal and said AV time interval is less than or equal to said predetermined time interval value;

determining whether said AV time interval is regular if said AV time interval is greater than said predetermined time interval value;

comparing the ventricular rate with a predetermined crossover rate value if said AV time interval is regular;

classifying the rhythm of the heart as a ventricular tachycardia if said ventricular rate is greater than or equal to said predetermined crossover rate value;

providing a lower rate limit of a first rate zone and a lower rate limit of a second rate zone, said lower rate limit of said second rate zone being greater than said lower rate limit of said first rate zone;

providing a lower rate limit of a third rate zone being greater than said lower rate limit of said second rate zone;

comparing said ventricular contraction rate with said lower rate limit of said third rate zone if said AV time interval is greater than or equal to said SAV time interval;

comparing said ventricular contraction rate with said lower rate limit of said second rate zone if said ventricular rate is less than said lower rate limit of said third rate zone;

delivering defibrillation pulses to the heart if said ventricular contraction rate is greater than said lower rate limit of said third rate zone;

delivering cardioverting pulses to the heart if said ventricular contraction rate is greater than said lower rate limit of said second rate zone and less than said lower rate limit of said third rate zone; and delivering pacing pulses to the heart if said ventricular contraction rate is less than said lower rate limit of said second rate zone.

19. A method for classifying cardiac arrhythmias and delivering therapy to the heart comprising the steps of:

sensing the electrical activity of an atrium and a ventricle of the heart;

determining the ventricular rate of contraction and the atrial rate of contraction;

comparing the ventricular rate with a preset threshold value;

comparing the ventricular rate with the atrial rate if the ventricular rate exceeds said preset threshold value;

classifying the rhythm of the heart as ventricular fibrillation or ventricular tachycardia if the ventricular rate is greater than the atrial rate;

computing the time interval between atrial contraction and ventricular contraction (AV);

comparing said AV time interval with a predetermined time interval value if said atrial rate is equal to said ventricular rate;

classifying the rhythm of the heart as a junctional tachycardia if said ventricular and atrial rates are equal and said AV time interval is less than or equal to said predetermined time interval value;

determining whether said atrial rate is regular if the ventricular rate is less than said atrial rate;

determining whether said ventricular rate is regular if said atrial rate is determined to be regular;

said steps of determining whether the atrial rate is regular and determining whether the ventricular rate is regular for establishing if the heart rhythm is sinus tachycardia or an atrial arrythmia;

further determining whether said AV time interval is regular if said ventricular rate is determined to be regular;

classifying the rhythm of the heart as an atrial arrhythmia if said step of further determining determines that said AV time interval is regular to confirm that the rhythm of the heart is an atrial arrhythmia;

providing a lower rate limit of a first rate zone and a lower rate limit of a second rate zone, said lower rate limit of said second rate zone being greater than said lower rate limit of said first rate zone;

providing a lower rate limit of a third rate zone being greater than said lower rate limit of said second rate zone;

comparing said ventricular contraction rate with said lower rate limit of said third rate zone if said AV time interval is determined to be irregular to determine if the rhythm of the heart is ventricular fibrillation;

comparing said ventricular contraction rate with said lower rate limit of said second rate zone if said ventricular rate is less than said lower rate limit of said third rate zone to determine if the heart is in a fast rhythm or an arrhythmia requiring a cardioverting shock;

delivering defibrillation pulses to the heart if said ventricular contraction rate is greater than said lower rate limit of said third rate zone;

delivering cardioverting pulses to the heart if said ventricular contraction rate is greater than said lower rate limit of said second rate zone and less than said lower rate limit of said third rate zone; and delivering pacing pulses to the heart if said ventricular contraction rate is less than said lower rate limit of said second rate zone.

20. A method for classifying cardiac arrhythmias and delivering therapy to the heart comprising the steps of:

sensing the electrical activity of an atrium and a ventricle of the heart;

determining the ventricular rate of contraction and the atrial rate of contraction;

comparing the ventricular rate with a preset threshold value;

comparing the ventricular rate with the atrial rate if the ventricular rate exceeds said preset threshold value;

classifying the rhythm of the heart as ventricular fibrillation or ventricular tachycardia if the ventricular rate is greater than the atrial rate;

computing the time interval between atrial contraction and ventricular contraction (AV);

comparing said AV time interval with a predetermined time interval value if said atrial rate is equal to said ventricular rate;

classifying the rhythm of the heart as a junctional tachycardia if said ventricular and atrial rates are equal and said AV time interval is less than or equal to said predetermined time interval value;

determining whether said atrial rate is regular if the ventricular rate is less than said atrial rate;

determining whether said ventricular rate is regular if said atrial rate is determined to be regular;

said steps of determining whether the atrial rate is regular and determining whether the ventricular rate is regular for establishing if the heart rhythm is sinus tachycardia or an atrial arrythmia;

further determining whether said AV time interval is regular if said ventricular rate is determined to be regular;

classifying the rhythm of the heart as an atrial arrhythmia if said step of further determining determines that said AV time interval is regular to confirm that the rhythm of the heart is an atrial arrhythmia;

further determining whether said AV time interval is regular if either one of said ventricular or atrial rates is determined to be irregular to identify the rhythm of the heart as sinus tachycardia or an atrial arrhythmia;

classifying the rhythm of the heart as an atrial arrhythmia with conduction problems if said step of further determining determines that said AV time interval is regular and otherwise classifying the rhythm of the heart as an atrial arrhythmia coincident with ventricular tachycardia or ventricular fibrillation;

providing a lower rate limit of a first rate zone and a lower rate limit of a second rate zone, said lower rate limit of said second rate zone being greater than said lower rate limit of said first rate zone;

providing a lower rate limit of a third rate zone being greater than said lower rate limit of said second rate zone;

comparing said ventricular contraction rate with said lower rate limit of said third rate zone if said step of further determining determines that said AV interval is irregular;

comparing said ventricular contraction rate with said lower rate limit of said second rate zone if said ventricular rate is less than said lower rate limit of said third rate zone;

delivering defibrillation pulses to the heart if said ventricular contraction rate is greater than said lower rate limit of said third rate zone;

delivering cardioverting pulses to the heart if said ventricular contraction rate is greater than said lower rate limit of said second rate zone and less than said lower rate limit of said third rate zone; and delivering pacing pulses to the heart if said ventricular contraction rate is less than said lower rate limit of said second rate zone.

21. A system for classifying cardiac arrhythmias and delivering therapy to the heart comprising:

sensing means for sensing the ventricular electrical activity and atrial electrical activity of the heart;

cardiac arrhythmia classifying means for:

determining the ventricular rate of contraction and the atrial rate of contraction based on said sensed ventricular and atrial electrical activity;

comparing the ventricular rate with a preset threshold value;

comparing the ventricular rate with the atrial rate if the ventricular rate exceeds said preset threshold value; and classifying the rhythm of the heart as ventricular fibrillation or ventricular tachycardia if the ventricular rate is greater than the atrial rate; and means for delivering therapy to the heart in the form of pacing pulses, cardioverting shocks or defibrillating shocks according to the classification of the rhythm of the heart.

22. The system of claim 21, wherein said cardiac arrhythmia classifying means:
   computes the time interval (AV) between atrial contraction and ventricular contraction;
   compares said AV time interval with a predetermined time interval value if said atrial rate is equal to said ventricular rate;
   declares that the heart is in a junctional tachycardia if said ventricular and atrial rates are equal and said AV time interval is less than or equal to said predetermined time interval value;

23. The system of claim 22, wherein said cardiac arrhythmia classifying means:
   determines whether said AV time interval is regular if said AV time interval is greater than said predetermined time interval value;
   compares the ventricular rate with a predetermined crossover rate value if said AV time interval is regular;
   declares that the heart is in a ventricular tachycardia if said ventricular rate is greater than or equal to said predetermined crossover rate value.

24. The system of claim 23, wherein said cardiac arrhythmia classifying means:
   determines the time interval (SAV) between sinus atrial contraction and ventricular contraction;
   compares said AV time interval with said SAV time interval;
   declares that the heart is in ventricular tachycardia if said AV time interval is greater than or equal to said SAV time interval and otherwise declares that the heart is in another condition.

25. The system of claim 23, wherein said cardiac arrhythmia computes the standard deviation of said time interval between atrial contraction and ventricular contraction, and in order to determine whether said time interval between atrial contraction and ventricular contraction, said cardiac arrhythmia classifying means:
   computes a predetermined fraction of said AV time interval;
   compares said standard deviation of said AV time interval; and
   declares said AV time interval to be regular if said standard deviation of said AV time interval is greater than or equal to said predetermined fraction, and otherwise declares said AV time interval to be irregular.

26. The system of claim 22, wherein said cardiac arrhythmia classifying means:
   determines whether said atrial rate is regular if said ventricular rate is less than said atrial rate;
   determines whether said ventricular rate is regular if said atrial rate is determined to be regular;
   determines whether said AV time interval is regular if said ventricular rate is determined to be regular;
   declares that the heart is in an atrial arrhythmia if said time interval between atrial contraction and ventricular contraction is regular.

27. The system of claim 26, wherein said cardiac arrhythmia classifying means:
   further determines whether said time interval between atrial contraction and ventricular contraction is regular if either one of said ventricular or atrial rates is determined to be irregular;
   declares that the heart is in an atrial arrhythmia with conduction problems if said AV time interval is regular and otherwise declaring that the heart is in an atrial arrhythmia coincident with ventricular tachycardia or ventricular fibrillation.

28. The system of claim 26, wherein said cardiac classifying means computes the standard deviation of said atrial contraction rate and said ventricular contraction rate; and in order to determine whether said atrial rate is regular, said cardiac arrhythmia classifying means:
   compares said standard deviation of said atrial contraction rate with a predetermined fraction of said atrial rate; and
   declares said atrial rate to be regular if said standard deviation of said atrial rate is less than said predetermined fraction of said atrial rate, and otherwise declares said atrial contraction rate to be irregular; and in order to determine if said ventricular rate is regular, said cardiac arrhythmia classifying means:
   compares said standard deviation of said ventricular contraction rate with a predetermined fraction of said ventricular contraction rate; and
   declares said ventricular rate to be regular if said standard deviation of said ventricular contraction rate is less than said predetermined fraction of said ventricular contraction rate, and otherwise declares said ventricular contraction rate to be irregular.

29. The system of claim 22, wherein said cardiac arrhythmia classifying means:
   provides a lower rate limit of a first rate zone and a lower rate limit of a second rate zone, said lower limit of said second rate zone being greater than said lower rate limit of said second rate zone;
   provides a lower rate limit of a third rate zone being greater than said lower rate limit of said second rate zone;
   compares said ventricular contraction rate with said lower rate limit of said third rate zone if said ventricular contraction rate is greater than said atrial contraction rate; and
   compares said ventricular contraction rate with said lower rate limit of said second rate zone if said ventricular rate is greater than said lower rate limit of said third rate zone.

30. The system of claim 29, wherein said means for delivering therapy to the heart comprises:
   pacemaking means for generating pacing pulses for delivery to the heart;
   pacing electrode means connected to said pacing means and implanted on or about the heart for applying said pacing pulses to the heart;
   cardioversion/defibrillation means for generating defibrillation pulses and cardioverting pulses for delivery to the heart;
   defibrillation electrode means connected to said defibrillation means and implanted on or about the heart for applying said defibrillation pulses and said cardioverting pulses through the heart; and
   wherein said cardiac arrhythmia classifying means:
      triggers said cardioversion/defibrillation means to delivery said defibrillation pulses to the heart if said ventricular contraction rate is greater than said lower rate limit of said third rate zone;
      triggers said cardioversion/defibrillation means to deliver said cardioverting pulses to the heart if said ventricular contraction rate is less than said lower rate limit of said third rate zone and greater than said lower rate limit of said second rate zone; and triggers said pacemaking means to deliver pacing pulses to the heart if said ventricular contraction rate is less than said lower rate limit of said second rate zone.

* * * * *